US006749841B2

United States Patent
Joshi et al.

(10) Patent No.: US 6,749,841 B2
(45) Date of Patent: Jun. 15, 2004

(54) STABILIZED AQUEOUS ACIDIC ANTIPERSPIRANT COMPOSITIONS AND RELATED METHODS

(75) Inventors: Vijay Kumar Joshi, Livingston, NJ (US); Philip Franco, Ocean Grove, NJ (US); Leandro Gimpaya Carpio, Staten Island, NY (US)

(73) Assignee: Revlon Consumer Products Corporation, New York, NY (US)

( * ) Notice: Subject to any disclaimer, the term of this patent is extended or adjusted under 35 U.S.C. 154(b) by 32 days.

(21) Appl. No.: 09/915,410

(22) Filed: Jul. 26, 2001

(65) Prior Publication Data

US 2003/0031638 A1 Feb. 13, 2003

(51) Int. Cl.$^7$ ................................................. A61K 7/32
(52) U.S. Cl. ............................ 424/65; 424/65; 424/66; 424/67; 424/80; 424/81; 424/401
(58) Field of Search .............................. 424/65, 66, 67, 424/80, 81, 401

(56) References Cited

U.S. PATENT DOCUMENTS

| | | | | |
|---|---|---|---|---|
| 2,230,084 A | 1/1941 | Montenier | ................... | 167/90 |
| 2,498,514 A | 2/1950 | Van Mater | ................... | 167/90 |
| 2,507,128 A | 5/1950 | Wainer | ................... | 167/90 |
| 2,814,585 A | 11/1957 | Daley | ................... | 167/90 |
| 3,991,176 A | 11/1976 | Rubino | ................... | 424/47 |
| 4,028,390 A | 6/1977 | Rubino | ................... | 260/429.3 |
| 4,148,812 A | 4/1979 | Rubino | ................... | 260/429.3 |
| 4,223,010 A | 9/1980 | Rubino | ................... | 424/66 |
| 4,650,671 A | 3/1987 | Golman | ................... | 424/66 |
| 4,719,102 A | 1/1988 | Randhawa | ................... | 424/66 |
| 4,722,835 A | 2/1988 | Schamper | ................... | 424/66 |
| 4,725,430 A | 2/1988 | Schamper | ................... | 424/66 |
| 4,816,261 A | 3/1989 | Luebbe | ................... | 424/65 |
| 5,066,485 A | * 11/1991 | Brieva et al. | ................... | 424/63 |
| 5,143,718 A | 9/1992 | Bar-shalom | ................... | 424/47 |
| 5,194,262 A | * 3/1993 | Goldberg et al. | ........... | 424/401 |
| 5,376,363 A | 12/1994 | Benefatto | ................... | 424/66 |
| 5,490,979 A | 2/1996 | Kasat | ................... | 424/66 |
| 5,508,028 A | * 4/1996 | Berschied, Jr. | ............... | 424/65 |
| 5,609,855 A | 3/1997 | Oh | ................... | 424/65 |
| 5,723,135 A | 3/1998 | Ford | ................... | 424/401 |
| 5,725,846 A | 3/1998 | Vu | ................... | 424/65 |
| 5,939,055 A | 8/1999 | Vu | ................... | 424/65 |
| 6,083,492 A | 7/2000 | Modi | ................... | 424/65 |
| 6,139,880 A | 10/2000 | Dolak | ................... | 424/650 |
| 6,171,581 B1 | 1/2001 | Joshi | ................... | 424/65 |
| 6,180,125 B1 | 1/2001 | Ortiz | ................... | 424/401 |

FOREIGN PATENT DOCUMENTS

| | | |
|---|---|---|
| WO | WO 98/43604 | 10/1998 |
| WO | WO 00/61094 | 10/2000 |

* cited by examiner

*Primary Examiner*—Sabiha Qazi
(74) *Attorney, Agent, or Firm*—Julie Blackburn

(57) ABSTRACT

A method for inhibiting loss of gel strength in an acidic aqueous based solid antiperspirant composition gelled with one or more polysaccharides comprising adding to said composition an effective amount of a gel degradation inhibitor and an acidic aqueous based solid antiperspirant composition containing at least one phase gelled with one or more polysaccharide gelling agents, wherein the improvement comprises including in the polysaccharide gelled phase at least one gel degradation inhibitor.

16 Claims, No Drawings

STABILIZED AQUEOUS ACIDIC ANTIPERSPIRANT COMPOSITIONS AND RELATED METHODS

TECHNICAL FIELD

The invention is in the field of antiperspirant compositions.

BACKGROUND OF THE INVENTION

Antiperspirant stick compositions are usually anhydrous. They are typically solidified with waxes or various other types of gelling agents such as fatty alcohols, amino acid amides, and the like. One problem with such sticks is that they may be greasy and leave an undesirable residue on underarms and clothing.

The traditional drawbacks with wax-based antiperspirant sticks are remedied with aqueous based antiperspirant sticks gelled with polysaccharide gellants as taught in U.S. Pat. Nos. 6,033,651 and 6,171,581. Such formulas are unique to the antiperspirant market. They provide superior wetness protection and provide a sheer, cool-feeling application on the skin with little or no residue. One problem with such sticks is that the polysaccharide gellants that contribute to the desirable tactile properties tend to lose gel strength over time, which in turn contributes to stick breakage. Gel strength is a measure of the strength of a gelled solid. In antiperspirant solid sticks the gel strength must be carefully monitored to provide a commercially acceptable product. If gel strength is too hard the stick does not have adequate payoff. If the gel strength is not adequate the stick will break too easily. To further complicate the situation, the gel strength of a stick immediately after manufacture may be adequate, but due to the interaction between the various ingredients found within the stick the gel strength decreases over time.

The need gap in the antiperspirant solid stick market is to produce a solid stick that exhibits superior efficacy, sheer application, and minimal residue. In order to be commercially acceptable such sticks must exhibit stability and long term gel strength.

It is an object of the invention to provide solid antiperspirant stick compositions having a long term gel strength.

It is a further object of the invention to provide a method for improving gel strength and inhibiting loss of gel strength in an aqueous acidic composition gelled with polysaccharide gellants comprising adding a gel strengthening effective amount of a gel degradation inhibitor.

SUMMARY OF THE INVENTION

The invention is directed to a method for inhibiting loss of gel strength in an acidic aqueous based solid antiperspirant composition gelled with one or more polysaccharides comprising adding to said composition an effective amount of a gel degradation inhibitor.

The invention is also directed to a method for preparing an aqueous based antiperspirant composition having improved gel strength comprising the steps of:

a) preparing a water phase by combining antiperspirant salts, one or more polysaccharide gellants, a gel degradation inhibitor, and water and heating to a temperature sufficient to form a homogeneous mixture;

b) preparing an oil phase by combining at least one oil with one or more compatible ingredients, c) emulsifying the water phase into the oil phase.

The invention is also directed to a method for preparing an aqueous based solid antiperspirant composition having improved gel strength comprising the steps of:

a) preparing a first aqueous phase comprised of antiperspirant salts, water, and a gel degradation inhibitor and mixing well to form a homogeneous solution, b) preparing a second aqueous phase comprising water and at least one polysaccharide gellant, c) preparing an oil phase comprising at least one oil in combination with one or more oil compatible ingredients, d) emulsifying the second aqueous phase (b) into the oil phase (c) to form an emulsion; and e) emulsifying the first aqueous phase (a) into the mixture of (d) to form a water and oil emulsion solid antiperspirant composition.

one or more polysaccharide gellants, and a gel degradation inhibitor and heating to a temperature sufficient to form a homogeneous mixture, The invention is also directed to acidic aqueous based solid antiperspirant composition gelled with one or more water soluble polysaccharide gelling agents, wherein the improvement comprises including in the water phase an effective amount of a gel degradation inhibitor in the form of a water soluble metal salt.

DETAILED DESCRIPTION

All percentages mentioned herein are percentages by weight unless otherwise indicated.

The pH values of the solutions are measured at 15% w/w @25° C.

The term "gel strength" means the strength of a gel composition measured in grams per centimeter squared (gm/cm$^2$). Preferably, the gel strength is measured using a TA.XT2i analyzer with a cylindrical probe having a diameter of 2 inches. A circle about 1 cm. in diameter and 1 cm. in height is cut from a gel and placed on a glass slide beneath the elevated probe. The machine is activated and the probe falls on gel. The gel strength of the sample is the maximum force in grams/cm$^2$ required to fracture the gel sample.

I. The Method of the Invention

Typically aqueous based solid antiperspirant sticks contain efficacious levels of astringent antiperspirant salts which are acidic in nature. The acidity contributes to the effectiveness of such salts in inhibiting perspiration. However, antiperspirant salts are very difficult to formulate because their inherent acidity reduces the pH of the stick which in turn may have a negative impact on other ingredients in the stick which may be pH labile. Increasing the pH of the antiperspirant stick by including other neutralizing ingredients in the stick, or reacting the antiperspirant salts themselves with a neutralizing agent, may reduce the incompatibility between the low pH salts and other ingredients in the stick but the effectiveness of the antiperspirant salts on inhibiting perspiration is then compromised. It has been discovered that antiperspirant salts that are too neutralized are not as effective in inhibiting perspiration. Thus, a certain balance must be maintained between formula stability and efficacy.

It has been found that aqueous based antiperspirant stick compositions gelled with polysaccharides are particularly susceptible to stick degradation, e.g. the sticks lose a significant amount of gel strength within one week (especially at elevated temperature) after they are poured because polysaccharide gellants readily hydrolyze in acidic media. Certain tests on such sticks show that the aqueous-based antiperspirant sticks gelled with polysaccharides lose as much as 33% of their original gel strength when stored at 40° C. for one week, and as much as 65% of their original gel strength when stored at 40° C. for five weeks. Typically the pH of these antiperspirant sticks is in the range of 3.2 to 3.5.

In the method of the invention, the loss in gel strength over time can be minimized by including at least one gel degradation inhibitor in the aqueous based antiperspirant compositions gelled with polysaccharides, preferably in the aqueous phase. Most suitable gel degradation inhibitors are those materials which are capable of increasing the pH of the antiperspirant composition to a range of about 4.2 to 4.5. Examples of suitable gel degradation inhibitors include water soluble inorganic or organic bases that are stable (i.e. do not precipitate the antiperspirant salts), and are capable of increasing the pH of the compositions at least ½ unit. The following materials may be suitable gel degradation inhibitors: salts of alkali and alkaline earth metals, urea, imidazole, tris buffers, N,N-tetrakis-2-hydroxypropyl-ethylenediamine, EDTA, alkali and alkaline earth metals reacted with amino acids, and so on. Further examples of such gel degradation inhibitors include sodium hydroxide, potassium hydroxide, zinc glycinate, and the like. Particularly preferred is zinc glycinate.

In a more preferred embodiment of the claimed method, the gel degradation inhibitor is added at certain times during manufacture of the compositions. In the case where the compositions are a single phase gel, the antiperspirant salts, agarose, water, and gel degradation inhibitor are combined and heated to 80° C. with stirring to dissolve all components until a clear solution is formed. The composition is poured into molds and allowed to cool. In preparing the single aqueous phase composition, it may be desirable to prepare the composition by combining all ingredients together and mixing well, preferably with elevated temperature.

It may also be desired to prepare separate phases of the single aqueous phase composition as a pre-mix, and then combine the separate pre-mixes together. For example, it is believed that the final composition exhibits improved stability when the single aqueous phase is prepared as two pre-mixes. The first pre-mix is an aqueous solution of antiperspirant salt and the gel degradation inhibitor. The second pre-mix comprises water, the polysaccharide gellant, and any other desired water soluble ingredients. The second pre-mix is then emulsified into the oil phase, which comprises at least one liquid oil and any other desired oil soluble ingredients. The first pre-mix is then emulsified into the emulsion. The resulting mixture is in the form of an emulsion with the water phase ingredients dispersed in the oil phase, or in the alternative where the oil phase is dispersed in the continuous water phase. The composition is poured into molds and allowed to cool.

While the preferred compositions made according to the claimed method are in the emulsion form, it may be desired to make single phase aqueous antiperspirant compositions. Such compositions are made by combining all of the aqueous phase ingredients and mixing well with heat to form a single homogeneous solution. The compositions are poured into molds to solidify. Alternatively, it may be desired to make two pre-mixes and then combine them to form the compositions. A first pre-mix is prepared by combining water, the antiperspirant salts, and the gel degradation inhibitor, and mixing well until a homogeneous solution is formed. A second pre-mix is prepared by combining water, the polysaccharide gellant, and any other desired water soluble ingredients and mixing with heat to form a homogeneous solution. Then the two pre-mixes are combined and mixed well and poured into appropriate containers.

In either case, the inclusion of the gel degradation inhibitor in the same water phase as the antiperspirant salts greatly enhances the stability of the product and causes significant inhibition in loss of gel strength. In a more preferable embodiment, the inhibitor is added during the manufacture of the antiperspirant active.

II. The Compositions

The invention is also directed to acidic aqueous based solid compositions gelled with one or more polysaccharides, wherein the improvement comprises inclusion of an effective amount of a gel degradation inhibitor.

A. Polysaccharide Gellants

The polysaccharide gellants used in the claimed compositions are present at about 0.05–50%, preferably about 0.1–40%, more preferably about 0.5–35% by weight of the total gel composition. The term "polysaccharide gellant" means a water soluble compound or composition (i) containing at least one saccharide moiety; and (ii) which, upon mixing with water in a ratio of about 1 to 1 at room temperature (25° C.) is capable of forming either a soft gel having a gel having a viscosity of about 1,000 to 800,000 centipoise at 25° C., and/or a gel strength of about 10 to 5,000 grams/cm$^2$ at 25° C. as measured using a TA.XT2i texture analyzer with a ½ inch diameter cylindrical probe. The term "saccharide moiety" means a polyhydroxy aldehyde or ketone, or acid hydrolysis product thereof, which, preferably, has the general formula $C_x(H_2O)_y$. Examples of saccharide moieties include the D and L forms of glucose, fructose, xylose, arabinose, fucose, galactose, pyruvic acid, succinic acid, acetic acid, galactose, 3,6-anhydro-galactose sulfate, galactose-4-sulfate, galactose-2-sulfate, galactose-2, 6-disulfate, mannose, glucuronic acid, mannuronic acid, guluronic acid, galactouronic acid, rhamnose, and so on. Preferably the polysaccharide gellants have a molecular weight ranging from about 500 to 15,000,000 daltons, preferably 5,000 to 1,000,000, more preferably 25,000 to 500,000 daltons. Polysaccharide gellants which fulfill the above criteria include polysaccharides such as galactans, galactomannans, glucomannans, polyuronic acids, and the like. Suitable galactans are agar, agarose, and kappa carageenan, iota carageenan, lambda carageenan. Examples of suitable galactomannans are locust bean gum and guar; examples of glucans are cellulose and derivatives thereof, starch and derivatives, dextrans, pullulan, beta 1,3-glucans, chitin, xanthan, tamarind and the like; examples of glucomannans are konjac; examples of polyuronic acids are algin, alginates, pectins; examples of heteropolysaccharides are gellan, welan, gum arabic, karaya gum, okra gum, aloe gum, gum tragacanth, gum ghatti quinceseed gum, psyllium, starch arabinogalactan and so on.

Preferred are galactans, in particular agarose, which is a polysaccharide comprised of basic repeating units of 1,3-linked beta-D-galactopyranose and 1,4-linked 3,6-anhydro-alpha-L-galactopyranose saccharide moieties. The agarose may be substituted by hydrophobic or hydrophilic groups. Examples of hydrophobic groups are alkoxy, in particular, methoxy. Examples of hydrophilic or polar groups are sulfate, pyruvate and the like. Examples of such substitutions are taught in Aoki, T. T.; Araki & M. Kitamikado; 1990, Vibrio sp. AP-2. *Eur. J. Biochem*, 187, 461–465, which is hereby incorporated by reference. The average molecular weight of agarose ranges between 35,700 and 144,000 daltons. The agarose suitable for use in the compositions of the invention may be from any suitable source or locale. For example an article authored by M. Lahaye and C. Rochas, *Hydrobiologia,* 221, 137–148, 1991, which is hereby incorporated by reference, discusses the numerous different types of agarose from different origins of seaweed species, all of which are suitable for use in the compositions of the invention. Also suitable for use in the compositions of the invention are chemically modified agaroses, such as those taught in an article authored by K. B. Guiseley in *Industrial Polysaccharides:Genetic Engineering, Structure/ Property Relations and Applications,* Edited by M. Yalpani, 1987, Elsevier Science Publishers, which is hereby incorporated by reference. The Guiseley article teaches methods for the chemical modification of agaroses to obtain optimum gelling properties. One example of modified agarose is a hydroethylated agarose which is sold under the brand names SeaPlaque and SeaPrep from FMC, Inc. In general, any modification of agarose which does not affect the helical conformation (i.e. which is obtained via linkage of the O6 and O4 of galactose to the O2 of 3,6-anhydrogalactose) will preserve the gelling capability.

In the most preferred embodiment of the invention, the composition contains at least two polysaccharide gellants, preferably a galactan and one gellant which is a galactomannan, glucan, glucomannan, polyuronic acid, or heteropolysaccharide. Agarose suitable for use in the compositions can be purchased from FMC Inc, under the tradenames Seakem LE and Seakem CLE.

B. Antiperspirant Active

The compositions of the invention contain 1–30%, preferably 5–25%, more preferably 10–22% by weight of the total composition of antiperspirant active salt.

The term "antiperspirant active salt" or "antiperspirant salt" means any compound or composition having antiperspirant activity, preferably astringent metallic salts such as the inorganic and organic salts of aluminum, zirconium, and zinc, and mixtures thereof. Particularly preferred are the aluminum and zirconium salts such as aluminum halides, aluminum hydroxide halides, zirconyl oxide halides, zirconyl hydroxy halides, and mixtures thereof. Aluminum salts include those of the formula:

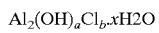

$$Al_2(OH)_aCl_b \cdot xH2O$$

wherein a is from about 2 to 5; a+b=6; x is from about 1 to about 6; and wherein a, b, and x may have non-integer values. Zirconium salts include those of the formula:

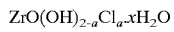

$$ZrO(OH)_{2-a}Cl_a \cdot xH_2O$$

wherein a is from about 1.5 to about 1.87; x is from about 1 to about 7; and wherein a and n may have non-integer values.

Examples of aluminum and zirconium salts include aluminum chloride, aluminum chlorohydrate, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum zirconium octachlorohdrate, aluminum zirconium octachloroydrex GLY, aluminum zirconium pentachlorohydrate, aluminum zirconium pentachlorohydrex GLY, aluminum zirconium tetrachlorohydrate, aluminum zirconium tetrachlorohydrex GLY, aluminum zirconium trichlorohydrate, aluminum zirconium trichlorohydrex GLY, and mixtures thereof.

Particularly preferred zirconium salts are those complexes also containing aluminum and glycine, in particular, aluminum zirconium tetrachlorohydrex GLY. The antiperspirant salts used in the composition of the invention are solubilized in the water. While preferably the antiperspirant salts are completely dissolved in the water, in some cases small amounts of salts may not be dissolved, i.e. may remain in the crystalline or suspensoid form.

C. Water

The compositions of the invention contain water in amounts ranging from about 1–90%, more preferably about 3–80%, most preferably about 5–60% water.

In one preferred embodiment of the invention the composition is clear or translucent, which means that the composition has a refractive index ranging from about 1.0 to 1.6, preferably 1.2 to 1.5 at 21° C. and an optical clarity of less than about 50 Nephelometric turbidity units (NTU) when measured with an Orbeco-Hellige #965 direct reading turbidometer, and a gel strength of 500 to 5000 grams/cm².

D. Gel Degradation Inhibitor

The compositions contain about 0.01–15%, preferably about 0.05–12%, more preferably about 0.1–10% by weight of the total composition of a gel degradation inhibitor. Suitable gel degradation inhibitors include water soluble organic or inorganic salts water soluble inorganic or organic bases that are stable (i.e. do not precipitate the antiperspirant salts), and are capable of increasing the pH of the compositions at least ½ unit. The following materials may be suitable gel degradation inhibitors: water soluble salts of alkali and alkaline earth metals, alkali and alkaline earth metal oxides, hydroxides, carbonates, bicarbonates, and trivalent metallic hydroxides, urea, imidazole, tris buffers, N,N-tetrakis-2-hydroxypropyl-ethylenediamine, ethylene diamine tetraacetic acid, and metal salts of amino acids, and so on. Particularly preferred is where the metal is salt is a metal salt of an amino acid glycine and the metal zinc.

E. Other Ingredients

The composition may also contain a variety of other ingredients that may improve the aesthetic or other features of the compositions, such as gel structure modifiers, humectants, preservatives, emollients and so on.

1. Gel Structure Modifiers

Preferably, the composition contains 1–50%, preferably 2–40%, more preferably 5–35% of at least on gel structure modifier. The term "gel structure modifier" means an ingredient which is capable of modifying the gel structure in some fashion; for example by plasticizing the gel structure, improving texture or moisturizing properties, which provide the end result of improving payoff when applied to the skin. For example, antiperspirant stick or gel compositions, when applied to the skin, must deposit a certain amount of product onto the skin. The amount of material deposited onto the skin as the gel is rubbed across the skin surface is called "pay off". If a gel does not have adequate pay off, when the gel is rubbed across the underarm skin, a sufficient amount of the gel composition will not rub off onto the skin. On the other hand, if the gel has too much pay off, when it is rubbed across the underarm skin too much of the gel deposits on the skin. Thus, it is important to regulate the gel structure and consistency so that pay off is optimal. Generally, suitable gel structure modifiers include polyols, aliphatic short chain mono-, di, and polyhydric alcohols, ethoxylated and/or propoxylated fatty alcohols or glycols, monomer and polymeric ethers and block copolymers, and the like.

a). Polyols

Suitable polyols are defined as compounds which contain three or more hydroxyl groups per molecule. Examples of suitable polyols include fructose, glucamine, glucose, glucose glutamate, glucuronic acid, glycerin, 1,2,6-hexanetriol, hydroxystearyl methylglucamine, inositol, lactose, malitol, mannitol, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, phytantriol, riboflavin, sorbeth-6, sorbeth-20, sorbeth-30, sorbeth-40, sorbitol, sucrose, thioglycerin, xylitol, and mixtures thereof.

b). Ethers

Also suitable as gel structure modifiers are homopolymeric or block copolymeric liquid ethers. Polymeric ethers are preferably formed by polymerization of monomeric alkylene oxides, generally ethylene or propylene oxides. Preferred monomeric ethers are those exhibiting the structure below were n=1. Preferred polymeric ethers are comprised of moieties having the general structure below wherein n=2 to 100:

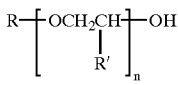

where R and R' are each independently H, or $C_{1-30}$ straight or branched chain alkyl, and n is 1 to 20. Examples of such polymeric ethers include PEG, PPG, PEG/PPG copolymers, and derivatives thereof as well as alkoxylated alcohols such as steareth 2–100, ceteth 2–100, and the like.

Other examples of suitable polymeric ethers include polyoxypropylene polyoxyethylene block copolymers having the general formula:

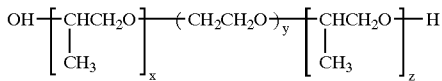

wherein x is 1–200, y is 1–200 and z is 1–200. Such compounds are sold under the CTFA name Meroxapol 105, 108, 171, 172, 174, 178, 251, 252, 254, 255, 258, 311, 312, and 314.

3. Alcohols

Mono- and dihydric alcohols are also suitable for use as gel structure modifiers. Generally, these mono- and dihydric alcohols have the general formula R(OH)N where n is 1 or 2 and R is a substituted or unsubstituted saturated $C_{2-10}$, preferably $C_{1-8}$ alkyl, or a substituted or unsubstituted alicyclic, bicyclic, or aromatic ring, with the substituents selected from halogen, alkoxy, hydroxy, and so on. Examples of suitable alcohols include monohydric alcohols such as ethanol, isopropanol, hexyldecanol, benzyl alcohol, propyl alcohol, and isopropyl alcohol, as well as dihydric alcohols such as hexylene glycol, diethylene glycol, ethylene glycol, propylene glycol, 1,2-butylene glycol, triethylene glycol, dipropylene glycol, methyl propanediol, and mixtures thereof 4. Sorbitan Derivatives Sorbitan derivatives, which are defined as ethers or esters of sorbitan, are also suitable gel structure modifiers. Examples of suitable sorbitan derivatives are the Polysorbates, which are defined as stearate esters of sorbitol and sorbitan anhydrides, such as Polysorbate 20, 21, 40, 60, 61, 65, 80, 81, and 85. Also suitable are fatty esters of hexitol anhydrides derived from sorbitol, such as sorbitan trioleate, sorbitan tristearate, sorbitan sesquistearate, sorbitan stearate, sorbitan palmitate, sorbitan oleate, and mixtures thereof 5. Organosiloxane Emulsifiers Also suitable as gel structure modifiers are organosiloxane emulsifiers, provided they are at least partially soluble in the aqueous single phase composition. Suitable organosiloxane emulsifiers generally contain at least one lipophilic radical or portion and at least one hydrophilic radical or portion so that a portion of the molecule is soluble in the aqueous phase composition and a portion of the molecule is dispersible in the aqueous phase composition. The polymeric organosiloxane used in the invention is preferably a liquid or semi-solid at 25° C. The polymeric organosiloxane is generally a water-in-oil or oil-in-water type surfactant which is preferably nonionic, having an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_w/M_o$$

where $M_w$ is the molecular weight of the hydrophilic group portion and $M_o$ is the molecular weight of the lipophilic group portion.

The term "organosiloxane polymer" means a polymer containing a polymeric backbone including repeating siloxy units that may have cylic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxy-polypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof The $C_{1-40}$ alkyl may be non-interrupted, or interruped by one or more oxygen atoms, a benzene ring, amides, esters, or other functional groups.

The polymeric organosiloxane emulsifier used in the invention may have any of the following general formulas:

$$M_xQ_y, \text{ or}$$

$$M_xT_y, \text{ or}$$

$$MD_xD'_yD''_zM$$

wherein each M is independently a substituted or unsubstituted trimethylsiloxy endcap unit, If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RR'SiO_{1.5}$ or $RRSiO_{1.5}$. Q is a quadrifunctional siloxy unit having the empirical formula $SiO_2$, and D, D', D'', x, y, and z are as set forth below, with the proviso that the compound contains at least one hydrophilic radical and at least one lipophilic radical. Examples of emulsifiers used in the compositions of the invention are of the general formula:

$$MD_xD'_yD''_zM$$

wherein the trimethylsiloxy endcap unit is unsubstituted or mono-substituted, wherein one methyl group is substituted with a lipophilic radical or a hydrophilic radical. Examples of such substituted trimethylsiloxy endcap units include $(CH_3)_2HPSiO$, $(CH_3)_2LPSiO$, $(CH_3)_2CH_2HPSiO$, $(CH_3)_2CH_2LPSiO$, wherein HP is a hydrophilic radical and LP is a lipophilic radical. D, D', and D'' are difunctional siloxy units substituted with methyl, hydrogen, a lipophilic radical, a hydrophilic radical or mixtures thereof In this general formula:

x=0–5000, preferably 1–1000 y=0–5000, preferably 1–1000, and z=0–5000, preferably 0–1000, with the proviso that the compound contains at least one lipophilic radical and at least one hydrophilic radical. Examples of these polymers are disclosed in U.S. Pat. No. 4,698,178, which is hereby incorporated by reference.

Particularly preferred is a linear silicone of the formula:

$$MD_xD'_yD''_zM$$

wherein $M=RRRSiO_{1/2}$

D and $D'=RR'SiO_{2/2}$ $D''=RRSiO_{2/2}$ x, y, and z are each independently 0–1000, where R is methyl or hydrogen, and R' is a hydrophilic radical or a lipophilic radical, with the proviso that the compound contains at least one hydrophilic radical and at least one lipophilic radical.

Most preferred is wherein

M=trimethylsiloxy $D=Si[(CH_3)][(CH_2)_nCH_3]O_{2/2}$ where n=1–40, $D'=Si[(CH_3)][(CH_2)_n-O-PE)]O_{2/2}$ where PE is $(-C_2HO)_a(-C_3H_6O)_bH$, o=0–40, a=1–100 and b=1–100, and $D''=Si(CH_3)_2O_{2/2}$ Organosiloxane polymers useful in the compositions of the invention are commercially available from Goldschmidt Corporation under the ABIL tradename including ABIL WE 09 or ABIL WS 08 which is cetyl dimethicone copolyol.

Another type of preferred organosiloxane emulsifier suitable for use in the compositions of the invention are emulsifiers sold by Union Carbide under the Silwet™ trademark. These emulsifiers are represented by the following generic formulas:

$$(Me_3Si)_{y-2}[(OSiMe_2)_{x/y}O-PE]_y$$

wherein $PE=-(EO)_m(PO)_nR$

R=lower alkyl or hydrogen

Me=methyl

EO is polyethyleneoxy

PO is polypropyleneoxy m and n are each independently 1–5000 x and y are each independently 0–5000, and $$Me_3SiO(Me_2SiO)_x(MeSiO)_ySiMe_3$$
$$|$$
$$PE$$

wherein $PE=-CH_2CH_2CH_2O(EO)_m(PO)_nZ$

Z=lower alkyl or hydrogen, and

Me, m, n, x, y, EO and PO are as described above, with the proviso that the molecule contains a lipophilic portion and a hydrophilic portion. Again, the lipophilic portion can be supplied by a sufficient number of methyl groups on the polymer backbone.

Particularly preferred is a Silwet™ polymer of the following general formula:

Wherein n is 1–10, preferably 8.

Another preferred organosiloxane emulsifier for use in the compositions of the invention is dimethicone copolyol.

Examples of other polymeric organosiloxane surfactants or emulsifiers include amino/polyoxyalkyleneated polydiorganosiloxanes disclosed in U.S. Pat. No. 5,147,578. Also suitable are organosiloxanes sold by Goldschmidt under the ABIL trademark including ABIL B-9806, as well as those sold by Rhone-Poulenc under the Alkasil tradename. Also, organosiloxane emulsifiers sold by Amerchol under the Amersil tradename, including Amersil ME-358, Amersil DMC-287 and Amersil DMC-357 are suitable. Dow Corning surfactants such as Dow Corning 3225C Formulation Aid, Dow Corning 190 Surfactant, Dow Corning 193 Surfactant, Dow Corning Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

Preferred is where the gel structure modifier is selected from a monomeric ether, polymeric ether, monohydric alcohol, dihydric alcohol, organosiloxane emulsifier, polymeric ether, or mixtures thereof. Particularly preferred is wherein the monohydric alcohol is a $C_{2-10}$ alkanol, preferably ethanol, and the dihydric alcohols are of the formula ROR' wherein each R and R' are independently H or a $C_{2-10}$ unsubstituted or substituted alkyl, where the substituent is hydroxyl or methyl; such compounds being preferably propylene glycol, dipropylene glycol, and methyl propandiol.

6. Deodorant Actives

It may be desired to incorporate into the cosmetic gel composition one or more deodorant actives. If so, a range of about 0.1–30% of deodorant active is suggested. The deodorant actives should be soluble in the aqueous single phase composition, or water dispersible carrier, such as triclosan encapsulated in cyclodextrin, which may be purchased from Lipo, Inc. Examples of suitable deodorant actives include fragrances, ammonium phenolsulfonate, benzalkonium chloride, benzethonium chloride, bromochlorophene, cetylpyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenolsulfonate, triclocarbone, triclosan, zinc phenolsulfonate, zinc ricinoleate, and mixtures thereof. The preferred deodorant active is triclosan, fragrance and the like.

The composition of the invention may contain other ingredients, providing such ingredients are soluble in the aqueous single phase composition, or water dispersible/miscible via emulsification or a delivery system. Such ingredients may possibly include humectants, detackifiers such as dimethyl isosorbide, preservatives, surfactants, and so on.

As noted, the single phase aqueous gel composition of the invention may be used alone, or it may be used to form an emulsion. In the latter case, the gel composition may either be dispersed into an oily phase, or the gel composition may form the continuous phase and the oily phase may be dispersed into the gel composition. The oily phase should be insoluble or immiscible with the aqueous gel phase. If the gel composition is used to form an emulsion, generally the emulsion composition will contain about 1–85%, preferably 5–70%, more preferably 7–60% by weight of the total emulsion composition of the aqueous single phase gel composition, and about 0.1–75%, preferably 0.5–65%, more preferably 1–50% by weight of the total emulsion composition of oil. Preferably, the emulsions are oil in water emulsions.

7. Oils

The oils used may be volatile or nonvolatile. The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20° C. Suitable volatile solvents generally have a viscosity of 0.5 to 10 centistokes at 25° C. Suitable volatile oils include linear silicones, cyclic silicones, paraffinic hydrocarbons, or mixtures thereof.

Cyclic silicones (or cyclomethicones) are of the general formula:

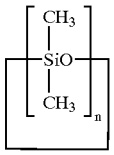

where n=3–7.

Linear volatile silicones in accordance with the invention have the general formula:

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Also suitable as the volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic ydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable. Transfer resistant cosmetic sticks of the invention will generally comprise a mixture of volatile silicones and volatile paraffinic hydrocarbons.

A wide variety of nonvolatile oils are also suitable for use in the cosmetic compositions of the invention. The nonvolatile oils generally have a viscosity of greater than 10 centipoise at 25° C., and may range in viscosity up to 1,000,000 centipoise at 25° C. Examples of nonvolatile oils suitable for use in the cosmetic sticks of the invention include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the *C.T.F.A. Cosmetic Ingredient Handbook*, First Edition, 1988, which is hereby incorporated by reference.

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Also suitable as the oil are various lanolin derivatives such as acetylated lanolin, acetylated lanolin alcohol, and so on.

Nonvolatile silicones, both water soluble and water insoluble, are also suitable as the oil component. Such silicones preferably have a viscosity of 10 to 600,000 centistokes, preferably 20 to 100,000 centistokes at 25° C. Suitable water insoluble silicones include amodimethicone, bisphenylhexamethicone, dimethicone, hexadecyl methicone, methicone, phenyl trimethicone, simethicone, dimethylhydrogensiloxane, stearoxytrimethylsilane, vinyldimethicone, and mixtures thereof.

Also suitable as the nonvolatile oil are various fluorinated oils such as fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

Guerbet esters are also suitable oils. The term "guerbet ester" means an ester which is formed by the reaction of a guerbet alcohol having the general formula:

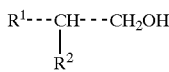

with a carboxylic acid having the general formula:

$R^3COOH$, or $HOOC—R^3—COOH$ wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil.

Preferably, the guerbet ester is a fluoro-guerbet ester which is formed by the reaction of a guerbet alcohol and a carboxylic acid (as defined above), and a fluoroalcohol having the following general formula:

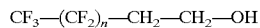

wherein n is from 3 to 40.

Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoamate. This ester is sold by Siltech, Norcross Ga. as Developmental Ester L61125A, under the tradename Silube GME-F.

Preferably, the compositions of the invention contain a mixture of volatile and nonvolatile silicone oils, so that the amount of volatile oil is about 1–10%, by weight of the total composition and the amount of nonvolatile oil is about 1–10% by weight of the total emulsion composition. In the preferred embodiment of the invention, the preferred volatile oil is cyclomethicone and the preferred nonvolatile oil is a low viscosity dimethicone i.e dimethicone having a viscosity of about 5–25 centipoise at 25° C.

8. Waxes

The oily phase of the emulsion may contain one or more materials that are solid at room temperature such as fatty acids, fatty alcohols, and the like. These materials act as gel structure modifiers for the oily phase. Suggested ranges of oily phase gel structure modifiers are 0.1–30%, preferably 0.5–25%, more preferably 1–20% by weight of the total emulsion composition. Suitable oily phase gel structure modifiers include straight or branched chain fatty alcohols having the formula R—OH wherein R is a straight or branched chain saturated or unsaturated alkyl having 6–30 carbon atoms. Such fatty alcohols include cetyl alcohol, stearyl alcohol, cetearyl alcohol, and the like. Also suitable are fatty acids having the formula R—COOH wherein R is a straight or branched chain saturated or unsaturated alkyl having 6–30 carbon atoms, which may be substituted with one or more hydroxyl groups. Preferred are fatty acids wherein R is straight or branched chain alkyl have 12–22 carbon atoms, which may be substituted with one or more hydroxyl groups. Particularly preferred is 12-hydroxystearic acid.

If the aqueous gel composition is combined with an oil phase to form an emulsion, the compositions prepared may be opaque, or clear or translucent. If clear, translucent compositions are desired, the oils selected should not be hazy or cloudy in appearance. Clarity is then achieved by matching the refractive indices of both phases such that they match within about 0.0001 to 0.0006.

The invention will be further described in connection with the following examples which are set forth for the purposes of illustration only.

EXAMPLE 1

An antiperspirant stick according to the invention was made as follows:

| Pre-mix A: | w/w % |
|---|---|
| PEG-14 dimethicone | 55.55 |
| Cyclomethicone, dimethicone crosspolymer (85/15) | 44.45 |

Pre-mix A was made by combining the ingredients and mixing well. Separately, pre-mix B was prepared as follows:

| Pre-mix B: | w/w % |
| --- | --- |
| Water | 47.57 |
| Dipropylene glycol | 21.94 |
| Agarose | 2.44 |
| Hydroxystearic acid | 14.63 |
| Premix A (from above) | 10.98 |
| Acetamide MEA (70% aqueous solution) | 2.44 |

Pre-mix B was made by combining water, dipropylene glycol, and agarose and heating the mixture to boil. When a clear solution is obtained the temperature of the mixture is lowered to 95° C. and hydroxy stearic acid is added with stirring till all the the hydroxy stearic acid has melted and uniformly mixed. At this stage premix A is added in increments with agitation. Finally acetamide MEA is added the mixture is maintained at 70 to 75° C., preferably between 65 to 70° C.

Then, 41 parts of Pre-mix B at 65 to 70° C. is mixed with 58 parts of aluminum zirconium tetrachlorohydrex gly pre-reacted with zinc glycinate heated to 45° C. to 50° C. The combined phases are mixed well so that the temperature of the final mixture is 55 to 65° C. and more preferably 54 to 58° C. After mixing for 3 minutes 1 part of fragrance is added to the mixture. The composition was poured into molds and cooled at ambient temperature until solidified.

We claim:

1. A method for inhibiting loss of gel strength in an acidic aqueous based solid antiperspirant composition gelled with one or more polysaccharides comprising the steps of:
    (a) heating a mixture of polysaccharides and water to obtain a homogeneous mixture,
    (b) separately heating the acidic antiperspirant active and a gel degradation inhibitor which is a metallic salt of an amino acid, to a temperature of about 45 to 50° C.
    (c) combining mixtures (a) and (b) to form a mixture having a temperature of 55 to 65° C.; and
    (d) cooling to room temperature.

2. The method of claim 1 wherein the composition is a water and oil emulsion.

3. The method of claim 1 wherein the gel degradation inhibitor increases the pH of the antiperspirant composition about ½ to 1 unit.

4. The method of claim 1 wherein the composition without the gel degradation inhibitor has a pH of about 3.2 to about 3.5 and after inclusion of the gel degradation inhibitor a pH of about 4.2 to 4.5.

5. The method of claim 1 wherein the gel degradation inhibitor is a zinc salt of an amino acid.

6. The method of claim 1 wherein the composition further comprises oil phase ingredients and is in the form of a water and oil emulsion.

7. The method of claim 6 wherein the oil phase ingredients are separately combined in a pre-mix, then added to the (a) mixture prior to addition of the (b) mixture.

8. The method of claim 7 wherein the pre-mix of oily phase ingredients is prepared by combining the ingredients and mixing.

9. The method of claim 8 wherein the oil phase ingredients include one or more volatile or nonvolatile oils.

10. The method of claim 9 wherein the volatile oil comprises a volatile silicone.

11. The method of claim 1 wherein the mixture (a) is heated to a temperature of about 100° C. to dissolve the polysaccharides in the water.

12. A method for inhibiting loss of gel strength in an acidic aqueous based solid antiperspirant composition in the water and oil emulsion form gelled with one or more polysaccharides comprising the steps of:
    (a) heating the polysaccharides and water to obtain a homogeneous mixture,
    (b) combining the oily phase ingredients and mixing well,
    (c) heating the acidic antiperspirant active and a gel degradation inhibitor which is a metallic salt of an amino acid, to a temperature of about 45 to 50° C,
    (d) combining mixtures (a) and (b) to form an emulsion; and
    (e) then adding mixture (c) to the mixture of (a) and (b); and
    (d) cooling to room temperature.

13. The method of claim 12 wherein the mixture (a) additionally contains one or more water soluble ingredients.

14. The method of claim 13 wherein the water soluble ingredients include glycols.

15. The method of claim 13 wherein the oily phase ingredients include one or more volatile oils.

16. The method of claim 13 wherein the temperature of the final mixture (e) ranges from about 54 to 65° C.

* * * * *